United States Patent
Singh et al.

(10) Patent No.: US 11,478,532 B2
(45) Date of Patent: Oct. 25, 2022

(54) THERAPEUTIC INTERVENTION FOR OSTEOPOROSIS

(71) Applicant: NATIONAL CENTRE FOR CELL SCIENCE, Pune (IN)

(72) Inventors: Kanupriya Singh, Pune (IN); Mohan Ramchandra Wani, Pune (IN)

(73) Assignee: NATIONAL CENTRE FOR CELL SCIENCE, Maharashtra (IN)

( * ) Notice: Subject to any disclaimer, the term of this patent is extended or adjusted under 35 U.S.C. 154(b) by 0 days.

(21) Appl. No.: 16/208,322

(22) Filed: Dec. 3, 2018

(65) Prior Publication Data

US 2019/0175700 A1   Jun. 13, 2019

(30) Foreign Application Priority Data

Dec. 3, 2017 (IN) .............................. 201721041260

(51) Int. Cl.
| | |
|---|---|
| *A61K 38/20* | (2006.01) |
| *A61P 19/08* | (2006.01) |
| *G01N 33/68* | (2006.01) |
| *G01N 33/50* | (2006.01) |

(52) U.S. Cl.
CPC ............ *A61K 38/202* (2013.01); *A61P 19/08* (2018.01); *G01N 33/5041* (2013.01); *G01N 33/6869* (2013.01); *G01N 33/6893* (2013.01); *G01N 2333/525* (2013.01); *G01N 2333/5403* (2013.01); *G01N 2800/10* (2013.01); *G01N 2800/108* (2013.01); *G01N 2800/50* (2013.01)

(58) Field of Classification Search
CPC ............. A61K 38/202; G01N 33/5041; G01N 2333/5403; G01N 2800/108
See application file for complete search history.

(56) References Cited

U.S. PATENT DOCUMENTS

| | | | |
|---|---|---|---|
| 6,384,194 B1 * | 5/2002 | Dorssers ............ | C07K 14/5403 424/85.2 |
| 6,861,257 B1 | 3/2005 | Maeda et al. | |
| 2016/0176927 A1 * | 6/2016 | Chung .................... | A61P 19/10 514/16.9 |

\* cited by examiner

*Primary Examiner* — Xiaozhen Xie (57) ABSTRACT

The present invention discloses a novel therapeutic intervention for osteoporosis. The present invention discloses that Interleukin-3 (IL-3) can be utilized as a therapeutic intervention against osteoporosis and for regulating bone homeostasis. The present invention also provides a method for determining the pre-disposition of a subject for osteoporosis by measuring the RANKL/OPG level.

11 Claims, 8 Drawing Sheets

THERAPEUTIC INTERVENTION FOR OSTEOPOROSIS

FIELD OF INVENTION

The present invention relates to the field of medicine. In particular, the present invention pertains to interleukin-3 as a possible therapeutic agent in osteoporosis.

BACKGROUND OF INVENTION

Remodelling in bone takes place throughout the life of an individual. The process of bone remodeling is regulated by the balanced interactions between bone resorbing osteoclasts and bone forming osteoblasts. Osteoclasts are giant multinucleated cells that originate from haematopoietic stem cells of monocyte/macrophage lineage. Osteoblasts are bone forming cells that differentiate from mesenchymal stem cells (MSCs).

Osteoclast pass through differentiation stages before finally maturing into a multinucleate bone resorbing osteoclast. The crucial factor for osteoclast differentiation is receptor activator of NF-B ligand (RANKL). RANKL is a 35 kDa protein found both as transmembrane glycoprotein on the surface of the cells and secreted soluble proteins. RANKL is expressed by various cell types such as activated T cells, mesenchymal cells, keratinocytes, B lymphocytes, mammary epithelial cells, vascular endothelial cells, cancer cells and microglia. The binding of RANKL to its receptor RANK on the surface of the osteoclast precursors initiate signals which lead to fusion, maturation, survival and activation of osteoclasts.

Cytokines secreted by immune and other cell types play an important role in regulation of bone remodelling. Interleukin-3 (IL-3), a cytokine secreted by activated T cells is a potent inhibitor of osteoclastogenesis and inhibits both RANKL and TNF-α-induced osteoclast formation and bone resorption. IL-3 also increases in vitro osteoblast differentiation and matrix mineralization from human MSCs; and enhances the ectopic bone formation in immunocompromised mice.

Osteoblast also secrete inhibitory proteins such as osteoprotegerin (OPG), which is a decoy receptor for RANKL that prevents binding of RANKL to RANK, thereby inhibiting osteoclast differentiation and activation. Alterations in the RANKL/OPG ratio modulate the bone remodeling in skeletal diseases such as osteoporosis, Paget's disease and osteoarthritis and also in ageing. Precise equilibrium between osteoblast and osteoclast activity is crucial to maintain the structural and functional integrity of bone, which is regulated by RANKL and OPG. Certain prior art also discloses the role of regulatory factors including cytokine in osteoclast and osteoblast modulation. US20160176927 discloses a peptide similar to that of natural IL-3, the peptide suppresses the activation of NF-κB and nuclear transition by inhibiting the RANKL-RANK signaling pathway, and suppresses the expression of a RANKL or an inflammatory cytokine-induced tartrate-resistant acid phosphatase (TRAP), cathepsin K, or TNF receptor type 1 or type 2, thereby inhibiting osteoclast differentiation depending on the treatment concentration. The peptide also contributes to osteoblast differentiation.

U.S. Pat. No. 6,861,257 discloses method for producing an osteoclast, by culturing osteoclast precursor cell in the absence of accessory cells in a culture medium comprising compound(s) IL-3, IL7, GM-CSF, eotaxin, eotaxin-2, and eotaxin-3. The osteoclast precursor cell is obtained by culturing a hematopoietic stem cell-derived cell obtained from peripheral blood or joint fluid of the patients.

Osteoporosis a medical condition in which the bones become brittle and fragile from loss of tissue, typically as a result of hormonal changes, or deficiency of calcium or vitamin D. It is estimated that about 1 in 3 women and 1 in 12 men over 45 years are at risk of suffering from osteoporosis.

Osteoporosis is typically treated by administering calcium, however, calcium is not absorbed adequately in old individuals. In some cases, estrogen or Parathyroid is indicated as an alternate therapy, however, long administration of hormones may lead to cancer of breast and ovary, in case of estrogen and other side effects. Calcitonin and biphosphonates are also administered, but they act only on bone resorption and do not restore the bone homeostasis. Furthermore, these therapies are costly and more often than not, they are not accessible to general patient population.

Though, there are certain studies centered on the pathophysiology of osteoclasts and osteoblasts in general, there are no studies demonstrating a therapeutic intervention of the pathology, especially in conditions of osteoporosis.

OBJECT OF THE INVENTION

An object of the present invention is to develop a novel therapeutic intervention for osteoporosis. The invention provides a pre-disposition test that identifies subjects that have an elevated risk for developing osteoporosis or osteoporosis-related conditions or diseases. In particular, the invention also provides a test based on the ratio of RANKL/OPG that identifies subjects at elevated risk for developing osteoporosis.

SUMMARY OF THE INVENTION

The present invention discloses a novel therapeutic intervention for osteoporosis. The present invention discloses that Interleukin-3 (IL-3) can be utilized as a therapeutic intervention against osteoporosis and for regulating bone homeostasis. The present invention also provides a method for determining the pre-disposition of a subject for osteoporosis by measuring the RANKL/OPG level.

BRIEF DESCRIPTION OF THE DRAWINGS

The application of the preferred embodiments of present invention is best understood with reference to the accompanying drawings, wherein.

DETAILED DESCRIPTION

The present invention discloses a novel therapeutic method for osteoporosis. The present invention discloses that Interleukin-3 (IL-3) can be utilized as a therapeutic intervention for osteoporosis.

In an embodiment, the present invention discloses that a subject having a bone metabolic disorder such as osteoporosis, pre-osteoporosis, and/or osteopenia may be advantageously treated by administering Interleukin-3.

The present invention discloses a method of treating osteoporosis comprising administering to a mammal therapeutically effective amount of interleukin 3 or a functional analogue thereof which retains the characteristics of interleukin 3.

The present invention discloses that interleukin 3 or any functional analog of interleukin 3 may be advantageously used for therapeutic intervention in osteoporosis. Preferably, the interleukin is human interleukin 3.

Figure 1:
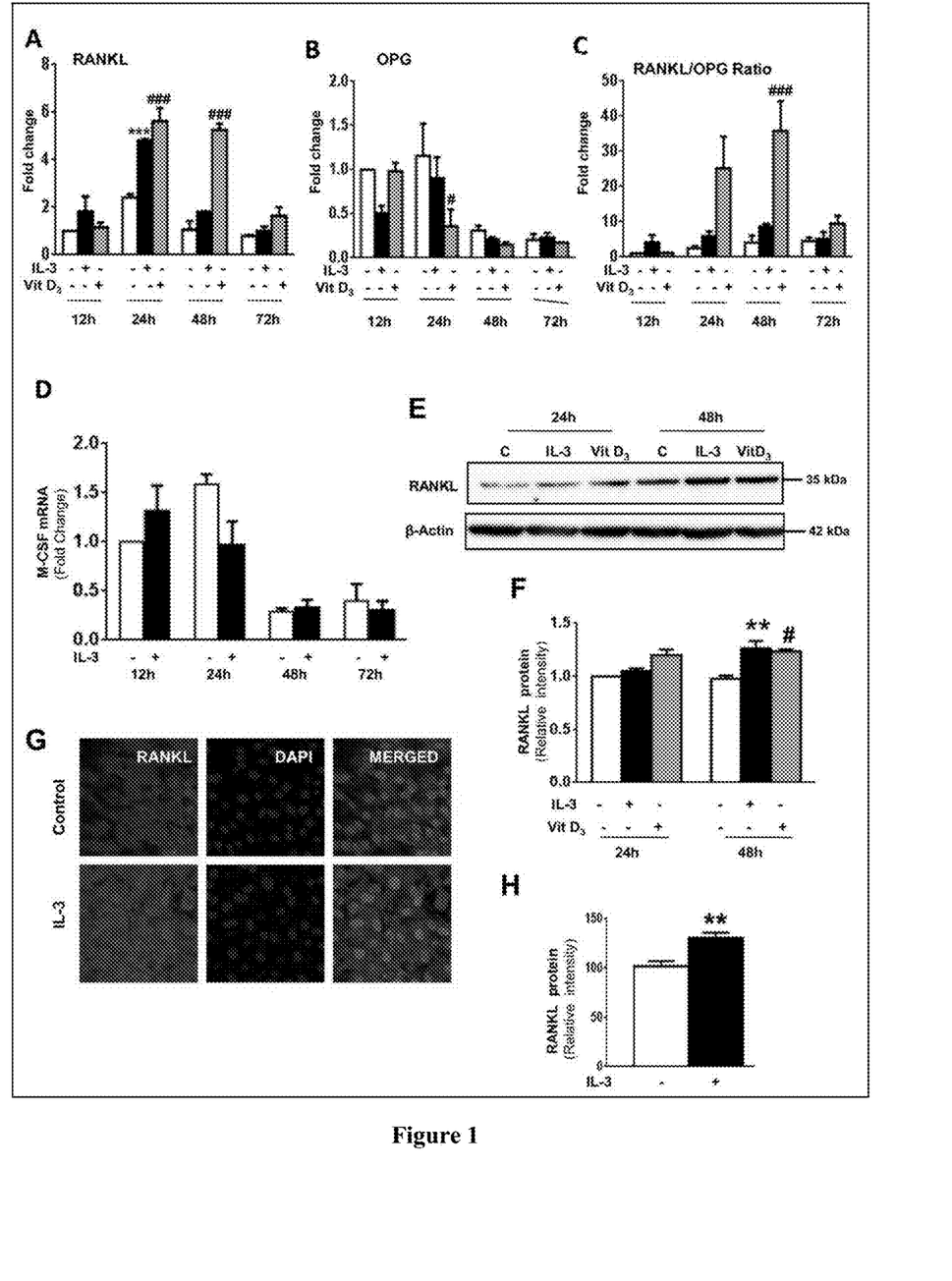
FIG. 1 depicts up-regulation of RANKL expression both at gene and protein level by IL-3.

Effect of IL-3 on RANKL Expression at Gene and Protein Levels in Calvarial Osteoblasts:

IL-3 has no toxic effect on calvarial osteoblasts. In order to determine, role of IL-3 on RANKL expression, mouse calvarial osteoblasts were cultured for 12, 24, 48 and 72 hours in α-MEM containing β-glycerophosphate (10 mM) and ascorbic acid (50 µg/ml) in absence or presence of recombinant mouse IL-3 (100 ng/ml) or vitamin D3 ($10^{-8}$ M) and gene expression of RANKL (A), OPG (B) and M-CSF (D) was determined by qPCR. The results are presented at FIG. 1. Results in (A), (B) and (D) are expressed as fold change of control. (C) represents the ratio of quantitative values of RANKL and OPG genes. Cells were also cultured for 24 and 48 hours in absence or presence of IL-3 or vitamin D3 and RANKL expression was analyzed by western blotting (E) and relative intensities (F) were calculated by densitometry using ImageJ software. Total RANKL protein expression was evaluated by immunofluorescence by culturing cells for 48 hours in absence or presence of IL-3 (G). Original magnification, ×63. Fluorescent intensity of RANKL expression was measured by using ImageJ software (H). Bar graphs are expressed as mean±SEM of three independent experiments. Significance was calculated by a one-way ANOVA followed by post hoc Bonferroni's multiple comparison test. $p<0.01$, *$p<0.001$ IL-3 versus untreated controls and #$p<0.05$, ###$p<0.001$ vitamin D3 versus untreated controls. From FIG. 1, it is evident that IL-3 significantly increases RANKL expression both at gene and protein levels.

IL-3 increased RANKL expression at all the time points and significant effect was seen at 24 hours in calvarial osteoblast (FIG. 1A) at gene level. Vitamin $D_3$ significantly enhanced RANKL expression at 24 and 48 hours. Vitamin $D_3$ significantly decreased OPG expression at 24 hours. However, IL-3 did not show any effect on OPG expression at all the time points (FIG. 1B). It was further observed that vitamin $D_3$ increased RANKL/OPG ratio at 24, 48 and 72 hours and significant effect was seen at 48 hours. Although, IL-3 increased RANKL/OPG ratio at all the time points, this effect of IL-3 was not significant (FIG. 1C). Effect of IL-3 in regulation of another glycoprotein such as M-CSF, which is also secreted by osteoblasts and required for survival and early stages of osteoclast differentiation, was evaluated. Similar to OPG, IL-3 showed no effect on expression of M-CSF at all the time points (FIG. 1D).

IL-3 also increased RANKL expression significantly at 48 hours at protein level. Vitamin $D_3$ increased RANKL expression at both 24 and 48 hours and significant effect was seen at 48 hours at protein level (FIGS. 1E and 1F). The effect of IL-3 on RANKL protein was further assessed by total protein expression at 48 hours by immunofluorescence microscopy. IL-3 significantly enhanced RANKL expression at protein level (FIG. 1G). FIG. 1H shows the fluorescence intensity of RANKL analysed by ImageJ software. The results thus suggest that IL-3 significantly increases RANKL at both gene and protein levels. However, IL-3 has no effect on proliferation of osteoblasts in a dose and time-dependent manner.

Effect of IL-3 on Osteoprotegerin

Figure 2:
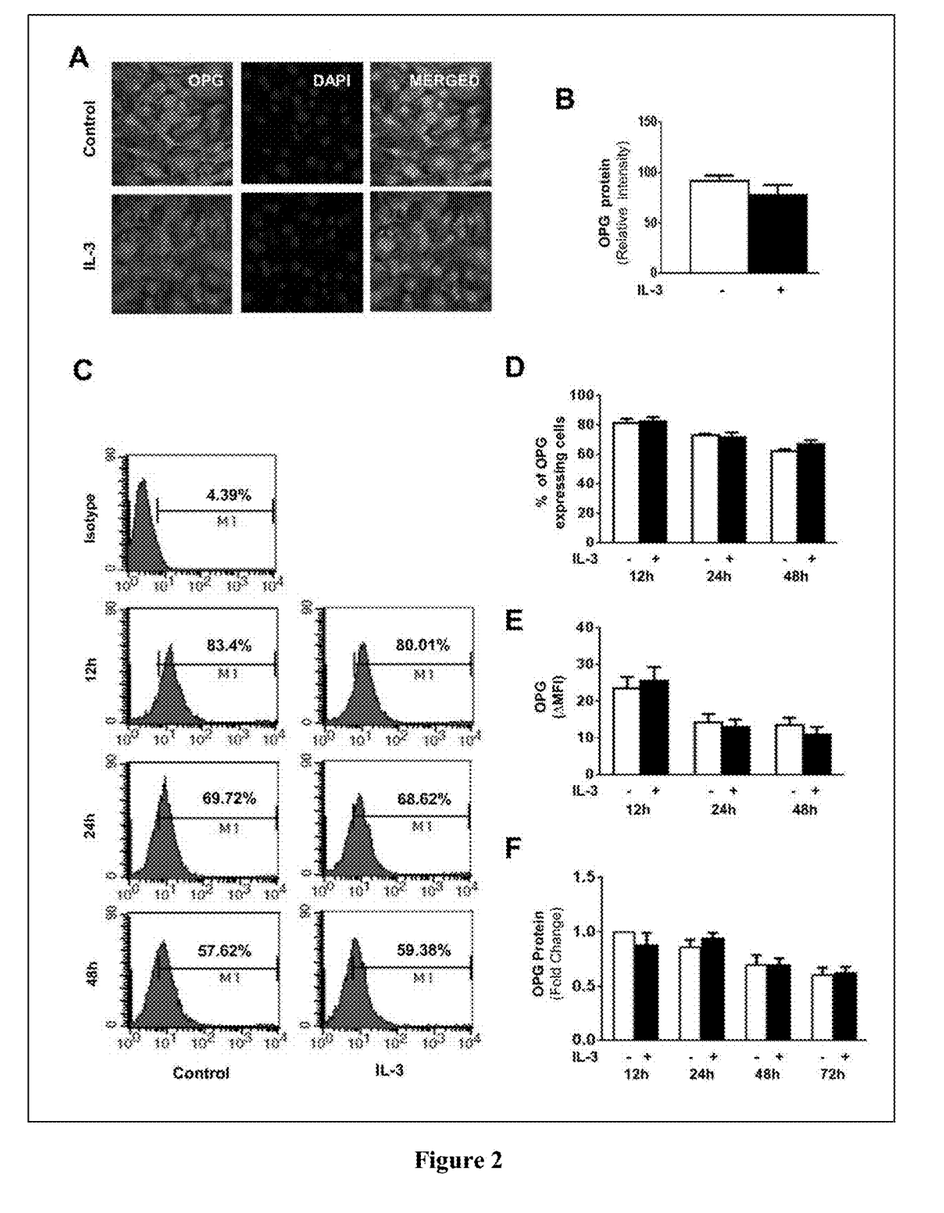
FIG. 2 depicts effect of IL-3 on OPG protein expression.

OPG protein expression was evaluated by immunofluorescence by culturing osteoblasts for 48 hours in absence or presence of IL-3. The results are presented at FIG. 2; 2(A) is at Original magnification, ×63. Fluorescent intensity of RANKL expression was measured by using ImageJ software (B). Calvarial osteoblasts were incubated for 12, 24, 48 and 72 hours in absence or presence of IL-3 (100 ng/ml) and analysis of intracellular OPG protein was done by flow cytometry (C). The data is representative of three independent experiments. (D and E) represents average percentage of OPG expressing cells and ΔMFI (change in mean fluorescence intensity) of three independent experiments. Bar graphs are expressed as mean±SEM of three independent experiments. (F) Cells were incubated for 12, 24, 48 and 72 hrs with IL-3 and secretion of OPG in culture supernatant was examined by ELISA. Results are average of four independent experiments. For the above it is evident that IL-3 has no effect on both intracellular and functional OPG expression. FIG. 2A and FIG. 2C shows that IL-3 has no effect on OPG expression at protein level. FIG. 2B represents fluorescence intensity of OPG protein expression. FIGS. 2D and 2E shows the average percentage of OPG expressing cells and ΔMFI (change in mean fluorescence intensity) respectively. The effect of IL-3 on functional secretary form of OPG was evaluated by incubating osteoblasts for 12, 24, 48 and 72 hours with IL-3 and OPG secretion in culture supernatant was analysed by ELISA. IL-3 showed no effect on OPG secretion at all the time points (FIG. 2F). These results confirm that IL-3 has no effect on both intracellular and functional OPG expression.

Effect of IL-3 on Osteoclasts and Differential Regulation of RANKL Expression by IL-3

Figure 3:
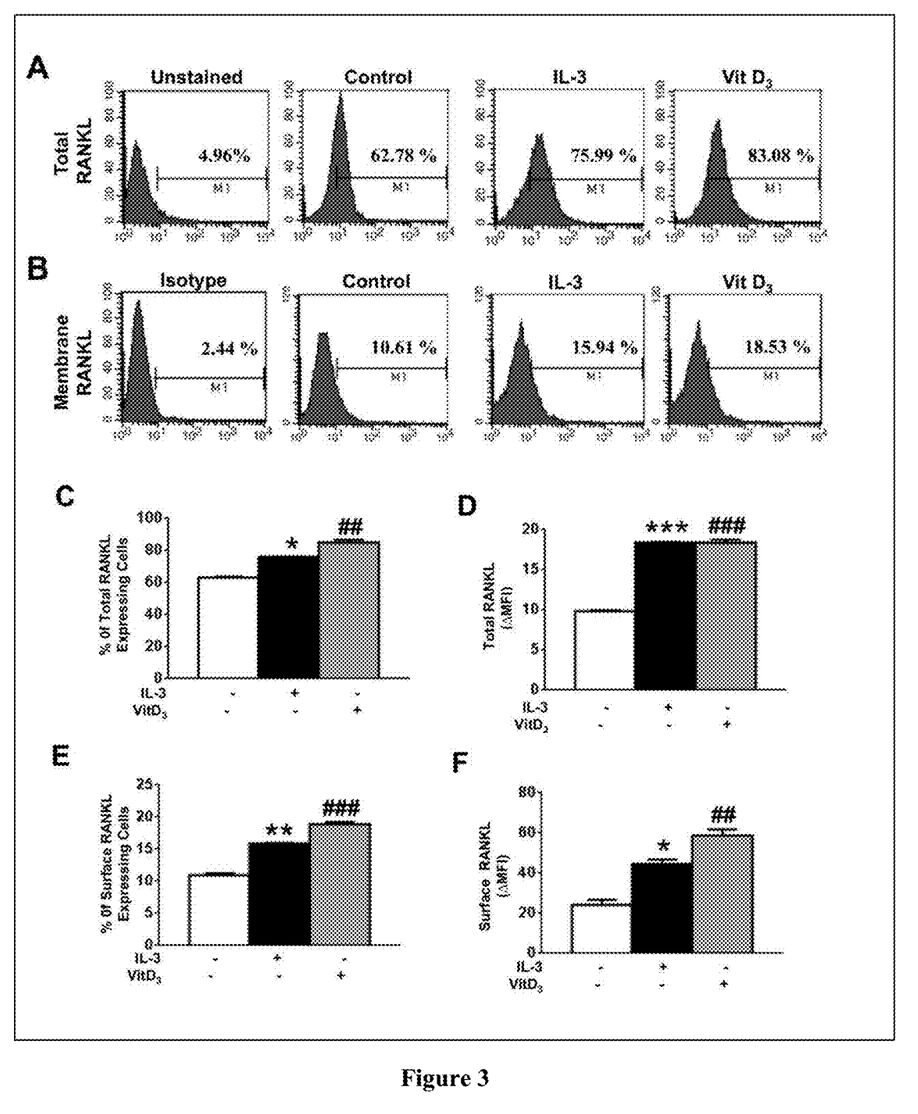
FIG. 3 depicts enhancement of membrane RANKL expression on osteoblasts by IL-3.
Figure 4:
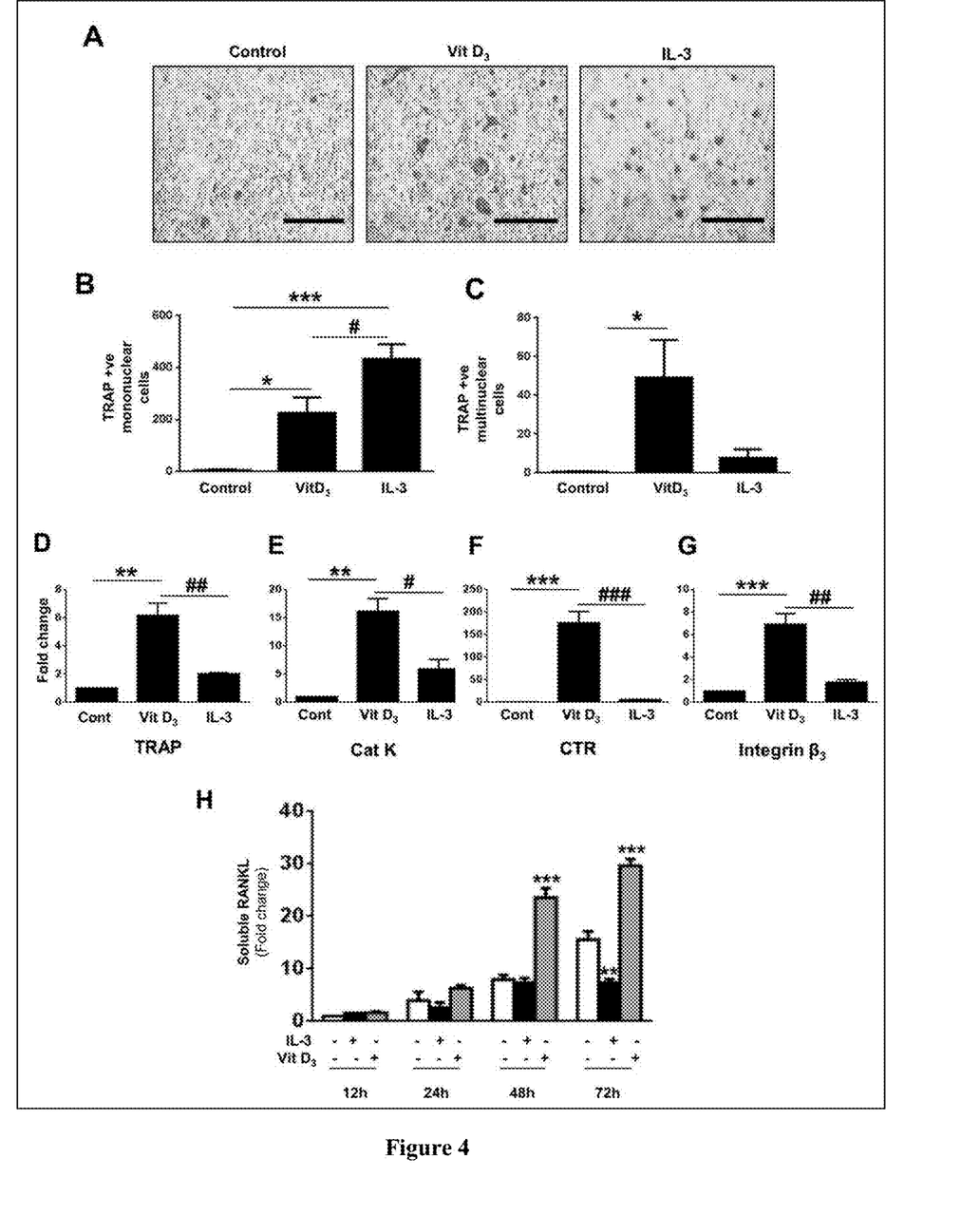
FIG. 4 depicts effect of IL-3 on osteoclast formation in co-culture model.

Effect of IL-3 on RANKL at functional level Calvarial osteoblasts were incubated with IL-3 or vitamin $D_3$ for 48 hours. The results are presented at FIG. 3 and total RANKL (A) and membrane bound (B) RANKL expression was analyzed by flow cytometry. FIGS. 3C and 3D shows the average percentage of cells and ΔMFI of total RANKL. FIGS. 3E and 3F shows the average percentage of cells and ΔMFI of membrane bound RANKL. Data is representative of three independent experiments. *$p<0.05$, $p<0.01$, *$p<0.001$ IL-3 versus untreated controls. ##$p<0.01$, ###$p<0.001$ vitamin $D_3$ versus untreated controls. Both IL-3 and vitamin D3 significantly increased expression of total and membrane RANKL (FIGS. 3A and 3B). FIGS. 3C and 3D shows the average percentage of cells and ΔMFI (change in mean fluorescence intensity) of total RANKL. FIGS. 3E and 3F shows the average percentage of cells and ΔMFI of membrane bound RANKL.

Effect of IL-3 on Osteoclast Differentiation and Secretion of Soluble RANKL

Mouse calvarial osteoblasts (2×10 cells/well) and bone marrow-derived M-CSF-dependent osteoclast precursors (2×10 cells/well) were cocultured in 48 well plates in absence or presence of IL-3 in a contact-dependent manner. (see FIG. 4) After 7 days cells were fixed with 10% formalin in PBS and stained for TRAP (A). Magnification, ×20. Scale bar, 200 μm. TRAP positive-mononuclear (B) and multinuclear (C) cells were counted. Vitamin $D_3$ ($10^{-8}$ mM) was used as positive control for induction of osteoclastogenesis. Gene expression analysis of osteoclasts specific markers such as TRAP (D), cathepsin K (E), calcitonin receptor (F) and integrin $β_3$(G) was done by real time PCR. Calvarial osteoblasts were cultured for 12, 24, 48 and 72 hrs with IL-3 or vitamin D3 and secretion of RANKL protein in culture supernatants was analyzed by ELISA (H). Data is average of two (B and C) or three (D-H) independent experiments. *$p<0.05$, $p<0.01$, *$p<0.001$ versus osteogenic media control. #$p<0.05$ for IL-3 treated versus Vitamin $D_3$ control. It can also be seen that Vitamin $D_3$ may induce formation of both TRAP-positive mononuclear and TRAP-positive multinuclear osteoclasts. IL-3 significantly increases TRAP-positive mononuclear osteoclasts but does not induce TRAP-positive multinuclear osteoclasts. The effect of IL-3 on osteoclasts specific genes such as TRAP, cathepsin K, calcitonin receptor and integrin $β_3$ in co-culture conditions was also assessed. The Vitamin D3 significantly increased soluble RANKL at 48 and 72 hours while IL-3 decreases secretion of soluble RANKL at 24 and 48 hours, and a significant decrease was seen at 72 hours (FIG. 4A-H). These results suggest that vitamin D3 increased both functional forms of RANKL. However, IL-3 increases membrane RANKL and decreases its soluble form; and hence, it was unable to induce mature osteoclasts formation in co-culture model.

Figure 5:
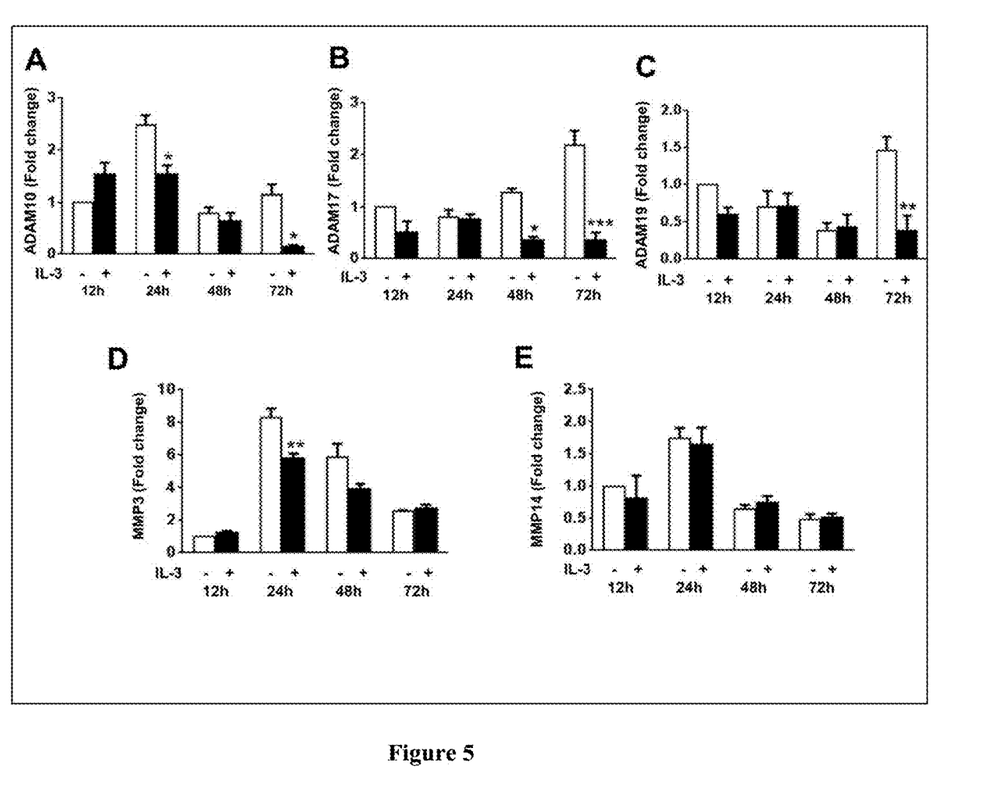
FIG. 5 depicts downregulation of the ectodomain shedding of membrane bound RANKL by IL-3.

From the above it is evident that the soluble RANKL is formed by the proteolytic cleavage of membrane bound RANKL. It is submitted that this process is called ectodomain shedding which is regulated by a) various ADAMs (a disintegrin and metalloproteinase) and b) MMPs IL-3 Differentially Regulates RANKL Expression Through Metalloproteases Calvarial osteoblasts were incubated for 12, 24, 48 and 72 hours with IL-3 and mRNA expression; of ADAM10 (A), ADAM17 (B) and ADAM19 (C); and MMP3 (D) and MMP14 (E) was examined by real-time PCR. Data is expressed as mean±SEM and bar graph represent average of three independent experiments. *$p<0.05$, $p<0.01$, *$p<0.001$ versus untreated controls. (See FIG. 5). To further investigate the mechanism of down-regulation of soluble RANKL by IL-3, osteoblasts were incubated for 12-72 hours with IL-3 and mRNA expression of ADAM10, ADAM17 and ADAM19 were examined by real time PCR. The effect of IL-3 on MMP3 and MMP14 expression was also assessed under similar culture conditions. The soluble RANKL is formed by the proteolytic cleavage of membrane bound RANKL. This process is called ectodomain shedding which is regulated by various ADAMs such as ADAM10, ADAM17 and ADAM19. MMPs such as MMP3 and MMP14 also play crucial role in ectodomain shedding of membrane RANKL. IL-3 significantly down-regulated the expression of ADAM10 at 24 and 72 hours (FIG. 5A). IL-3 significantly decreased ADAM17 expression at 48 and 72 hours, which is the main metalloproteases that regulate production of soluble RANKL from its membrane form (FIG. 5B); and also decreases ADAM19 expression at 72 hours (FIG. 5C). Besides ADAMs, IL-3 significantly decreases MMP3 expression at 24 hours (FIG. 5D) and showed no effect on MMP14 gene expression (FIG. 5E).

These results suggest that although IL-3 is capable of increasing RANKL expression at transcript and membrane bound protein levels, it decreases soluble RANKL by down-regulation of metalloproteases that eventually hinder the cleavage of soluble RANKL from its membrane form.

Figure 6:
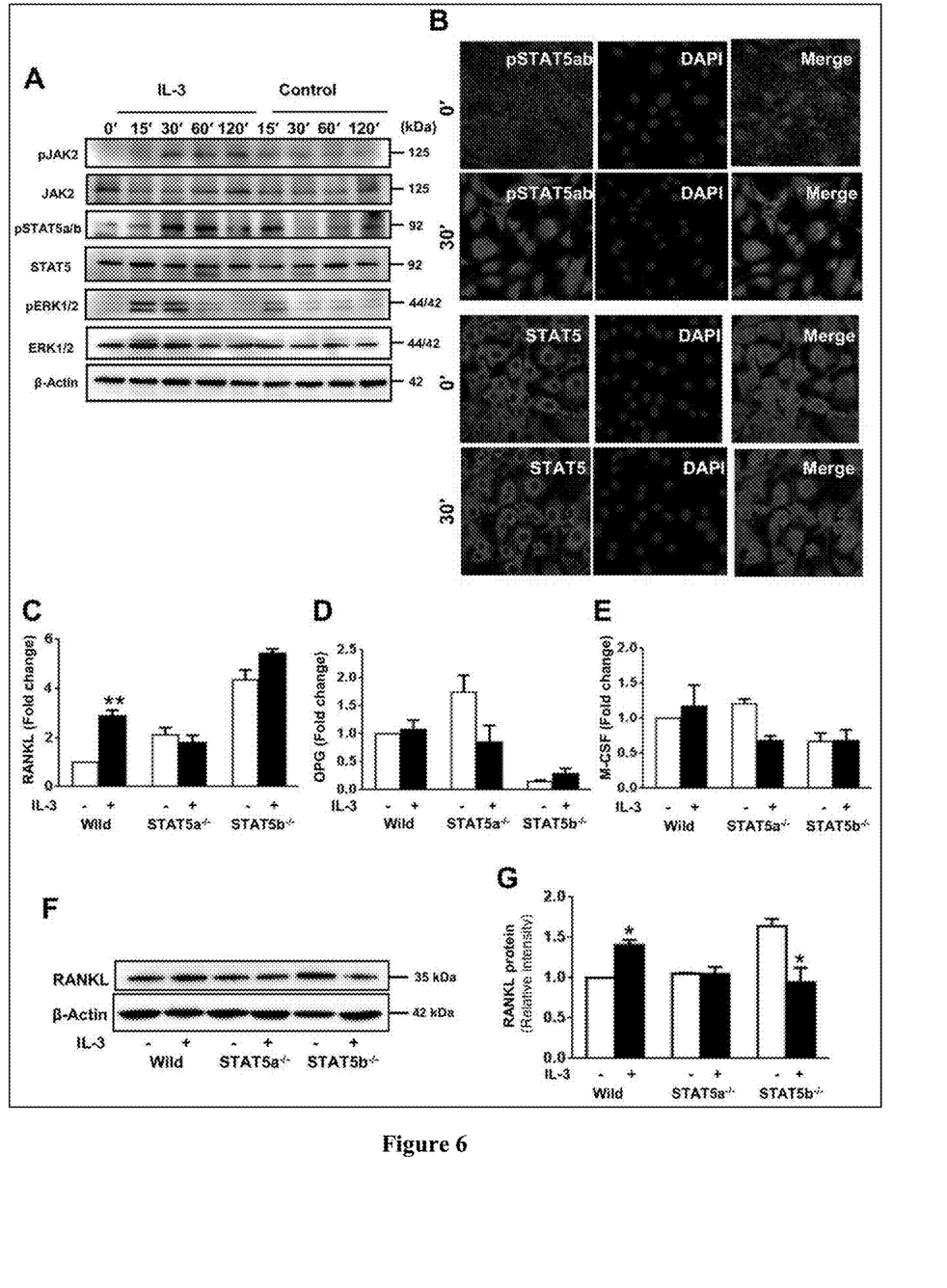
FIG. 6 depicts regulation of RANKL expression through JAK2/STAT5 pathway by IL-3.

IL-3 Activates Jak2/STAT5 Pathway and Regulates RANKL Expression Through STAT5 Isoform The role of JAK2/STAT5 pathway was also elucidated and presented at FIG. 6. Cells were cultured for 0, 15, 30, 60 and 120 minutes in presence of IL-3 (100 ng/ml) and activation of JAK2. STAT5 and ERK was evaluated by western blotting (A). Cells were cultured with IL-3 for 30 minute and analysis of STAT5 translocation was evaluated by immunofluorescence (B). Original magnification, ×63. AT-MSCs isolated from wild type, STAT5a and STAT5b knockout mice were cultured for 24 hours with IL-3 and expression of RANKL (C), OPG (D) and M-CSF (E) mRNA was evaluated by real-time PCR. RANKL protein expression was evaluated by Western blotting at 48 hours (F). Relative intensities were calculated by densitometry using ImageJ software (G). Data is representative of three (A and B) and two (F) independent experiments. Bar graph expressed as average of three (C to E) or two (G) independent experiments. *$p<0.05$, **$p<0.01$ IL-3 versus untreated controls. Thus from the above it is evident that STAT5a isoform plays a crucial role in IL-3 regulation of RANKL expression. IL-3 increases the membrane RANKL by activating Janus kinase2/Signal transducer and activator of transcription 5 (JAK2/STAT5) pathway by increasing phosphorylation of STAT5a and STAT5b. The above method may be utilized for physiological and diagnostic intervention in bone disorders. IL-3 phosphorylates JAK2 at 30, 60 and 120 minutes; and STAT5a/b at 30 and 60 minutes (FIG. 6A). We observed that IL-3 also increases phosphorylation of ERK1/2 in osteoblasts (FIG. 6A). These results indicate that IL-3 stimulates phosphorylation of STAT5 by both JAK2 and ERK1/2 dependent pathways. STAT5 transcription factor regulate expression of various genes. IL-3 increases the translocation of phospho STAT5 into the nucleus (FIG. 6B). Thus, IL-3 activates STAT5 via JAK2 and also induces its translocation into nucleus. RANKL expression is regulated by JAK2/STAT5a in mammary epithelial cells; and IL-3 increase phosphorylation of both isoforms of STAT5.

IL-3 increased RANKL expression at mRNA (FIG. 6C) and protein (FIGS. 6F and 6G) levels in wild type AT-MSCs, but showed no change in RANKL expression in STAT5a knock out AT-MSCs. IL-3 treated cells from STAT5b knockout mice showed no effect on RANKL expression at mRNA level (FIG. 6C) but significantly decreased RANKL expression at protein level (FIGS. 6F and 6G). No comparative effect of IL-3 was observed on OPG and MCSF expression between wild type, STAT5a and STAT5b knockout mice (FIGS. 6D and 6E). Thus STAT5a play a crucial role in IL-3 regulation of RANKL expression.

In Vivo Age Associated Changes in RANKL Expression

Figure 7:
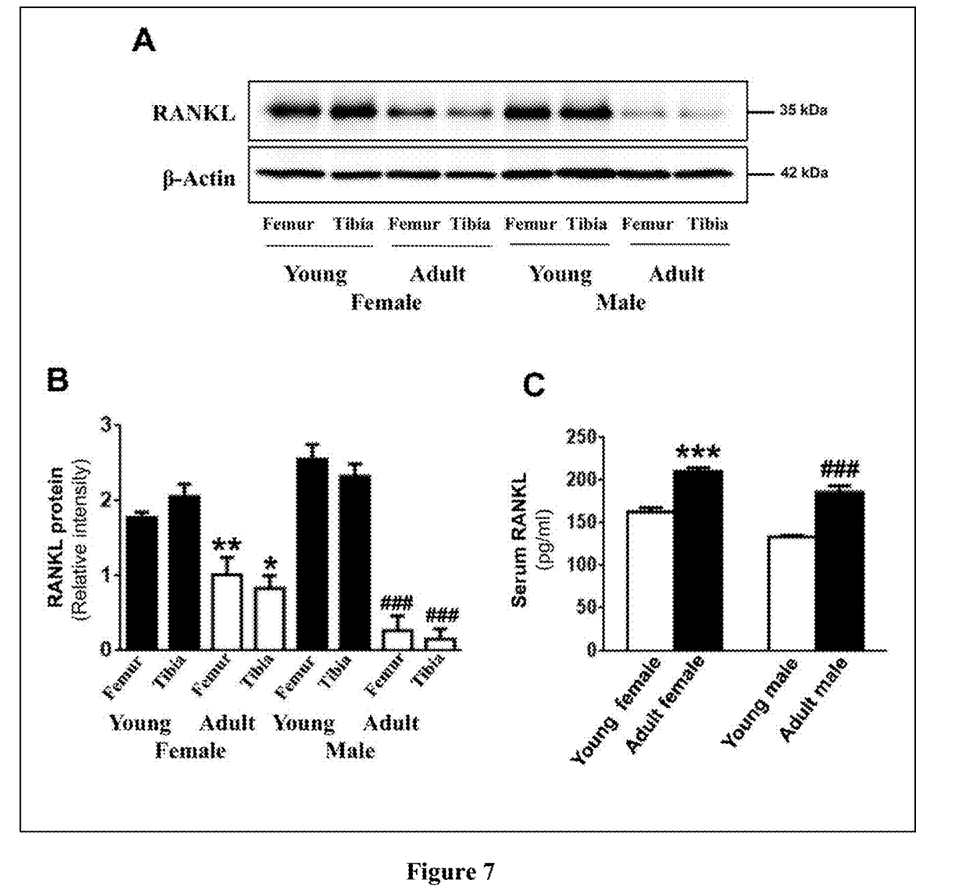
FIG. 7 depicts in vivo age associated changes in RANKL expression.

Change in bone tissue and serum specific RANKL expression was analyzed by western blotting (A) and ELISA (C) respectively, in female and male young mice of three months old and adult mice of one year old. (B) represents relative intensity of RANKL measured by densitometry using ImageJ software. Data is expressed as mean±SEM (n=5). *$p<0.05$, $p<0.01$, *$p<0.001$ adult versus young female mice and ###$p<0.001$ adult versus young male mice. (See FIG. 7). Since IL-3 regulates RANKL expression differentially in vitro in osteoblasts, the in vivo effect of IL-3 on RANKL and OPG modulation was analyzed. RANKL and OPG expression in young and adult female and male mice was compared. After removal of bone marrow, femur and tibia bones were used to analyze the expression of bone specific RANKL. Serum was used to analyze the soluble RANKL. The bone specific RANKL expression was significantly decreased in both adult female and male mice as compared to young mice (FIG. 7A). FIG. 7B represents the relative intensity of immunoblots measured by ImageJ software. The serum RANKL expression was significantly increased in both adult female and male mice (FIG. 7C). These results suggested the differential regulation of RANKL expression in adult mice.

In Vivo Role of IL-3 on Regulation RANKL/OPG Ratio in Adult Mice

Figure 8:
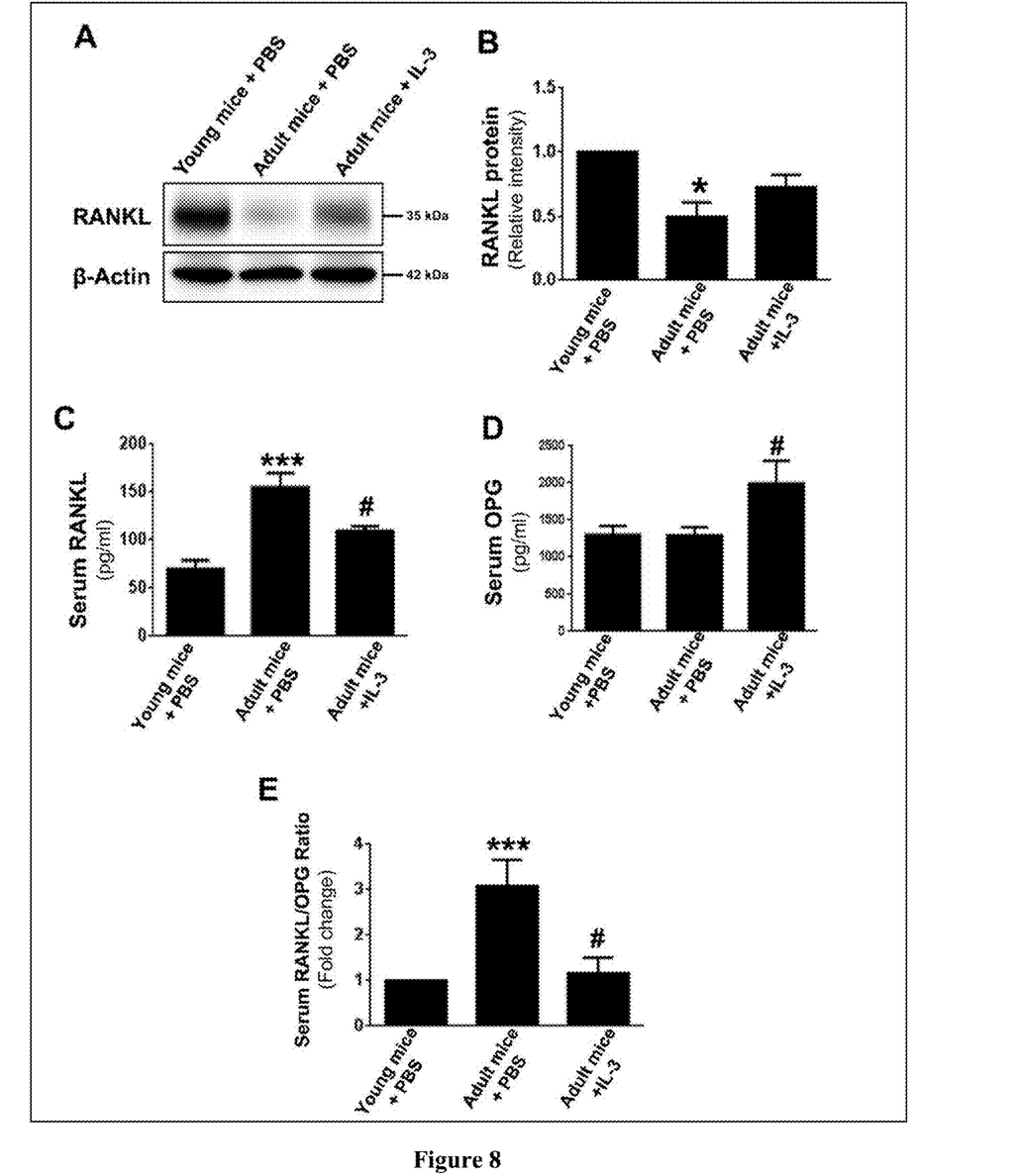
FIG. 8 depicts in vivo role of IL-3 on regulation RANKL/OPG ratio in adult mice.

Adult male mice were injected intra-peritoneally with PBS or IL-3 (3 μg/mice/day) for 5 days. Young mice injected with PBS were used as a control. The results are presented at FIG. 8. Changes in bone associated RANKL expression is measured by western blotting (A). Relative intensity (B) was calculated by densitometry using ImageJ software. Serum RANKL (C) and OPG (D) were measured by ELISA. (E) represents serum RANKL/OPG ratio. Bar graphs are expressed as mean±SEM (n=5). *$p<0.05$, ***$p<0.001$ adult versus young male mice and #$p<0.05$. IL-3 versus adult male mice. Although both female and male mice show similar changes in RANKL expression associated with bone and serum, to evaluate the role of IL-3 on RANKL, male mice were selected over female mice to avoid age related hormonal changes. Adult male mice were injected intraperitoneally with PBS or IL-3 (3 μg/mouse/day) for 5 days. Young mice injected with PBS were used as a control to compare the age related changes in RANKL Immunoblotting analysis showed significant decrease in bone specific RANKL in adult mice and it was markedly increased by IL-3 (FIG. 8A). FIG. 8B represent the relative quantitative analysis of immunoblots. Interestingly, IL-3 significantly decreased RANKL and increased OPG in serum of adult mice (FIGS. 8C and D). Furthermore, increased RANKL/OPG ratio in adult mice was decreased by IL-3 (FIG. 8E). All these results indicate that IL-3 help in restoring the disturbed RANKL and OPG expression in adult mice.

In another embodiment, the present invention discloses a method with a predetermined level of predictability for assessing a risk of development of osteoporosis, pre-osteoporosis, or bone fracture in a subject comprising:
  i. determining the ratio between RANKL/OPG levels;
  ii. measuring a clinically significant alteration in the RANKL/OPG levels;
  iii. Assessing predisposition to osteoporosis, increased risk of developing osteoporosis, pre-osteoporosis, or bone fracture in the subject from step (ii).

In yet another embodiment, the present invention discloses a novel molecule/drug for modulation of osteoclastogenesis and stimulatory and inhibitory proteins involved in pathophysiology of bone remodeling, comprising the steps of;
  i. isolating the osteoblasts;
  ii. assessing the effect of IL-3 on expression of stimulatory and inhibitory proteins in the osteoblasts obtained from step i) at both gene and protein levels;
  iii. assessing the of effect of IL-3 on total and membrane bound stimulatory protein RANKL in osteoblasts obtained from step ii) by flow cytometry and enzyme linked immunosorbent assay (ELISA);
  iv. assessing the role of IL-3 on expression of stimulatory and inhibitory proteins in vivo.
  v. isolating osteoclasts precursors;
  vi. co-culturing the osteoblasts and osteoclast precursors obtained from step i) and (v) with cytokine;
  vii. studying the effect of IL-3 in osteoclasts obtained from step vi.

The process is enumerated herein below and by way of examples:

Isolating the Osteoblasts

Mouse calvarial osteoblasts may be isolated from 2 to 5 days old BALB/c mice using modified sequential digestion method.

Assessing Expression of Stimulatory and Inhibitory Proteins in the Osteoblast Cells Obtained from Step i) at Both Gene and Protein Levels;

Mouse calvarial osteoblasts were cultured on glass coverslips in 24-well plates in the absence or presence of IL-3 for indicated time points. Staining for RANKL, OPG and IL-3Rα may be carried out using primary antibodies followed by fluorochrome conjugated secondary antibodies and viewed with a confocal microscope. Assessment and quantification of IL-3Rα expression on osteoblasts may be carried out by flow cytometry analysis. The effects of IL-3 on RANKL and OPG in a time-dependent manner were evaluated by culturing calvarial osteoblasts (for 12-72) hours in osteogenic media in absence or presence of IL-3 (50-500 ng/ml) or vitamin $D_3$ ($10^{-1}$-$10^{-8}$M). Expression of RANKL and OPG may be examined by quantitative real time PCR. Vitamin $D_3$ may be used as a positive stimulator of RANKL expression. To assess the effect of IL-3 on RANKL at protein level, osteoblasts were cultured for 24 and 48 hours with IL-3 or vitamin $D_3$, and expression of RANKL was evaluated by immunoblotting and relative intensity was analysed by ImageJ software. OPG protein was also evaluated by immunofluorescence by culturing osteoblasts for 48 hours with IL-3 and by flow cytometry by culturing cells for 12-48 hours with IL-3.

The effect of IL-3 on functional form of OPG expression is confirmed at protein level. The effect of IL-3 on functional secretary form of OPG may be evaluated by incubating osteoblasts for 12-72 hours with IL-3 and OPG secretion in culture supernatant may be analysed by ELISA.

Expression of RANKL, OPG, M-CSF, TRAP, Cathepsin K, calcitonin receptor, integrin $β_3$ and GAPDH may be assessed by real time PCR analysis The cytokine may be selected from a group comprising M-CSF, granulocyte macrophage macrophage-colony stimulating factor (GM-CSF) and IL-3 preferably IL-3. The stimulatory factor may be selected from a group comprising M-CSF and RANKL preferably RANKL. The inhibitory protein may be osteoprotegerin (OPG).

The gene expression of RANKL and OPG were assessed by polymerase chain reaction (PCR) and immunoblotting. IL-3 significantly increases RANKL expression both at gene and protein levels. IL-3 does not change osteoprotegerin level.

Assessing Total and Membrane Bound Stimulatory Protein RANKL in Osteoblasts Obtained from Step ii) by Flow Cytometry.

Osteoblasts may be incubated for 48 hours with IL-3 or vitamin $D_3$ and expression of total and membrane bound RANKL were analysed by flow cytometry. Further the effect of IL-3 on soluble form of RANKL was analyzed by the secretion of its soluble form in culture supernatants of osteoblasts culture incubated with IL-3 and vitamin $D_3$ for 12-72 hours. Soluble RANKL in culture supernatant may be analysed by ELISA.

Assessing the Role of IL-3 on Expression of Stimulatory and Inhibitory Proteins In Vitro.

Isolating the Osteoclast Precursors

Stromal cells free and M-CSF-dependent osteoclast precursors may be isolated from femoral and tibial bones. The effect of IL-3 may be assessed on osteoclast differentiation in co-culture model. The mouse calvarial osteoblasts 1-4× $10^4$ cells/well and bone marrow-derived osteoclast precursors (1-4×$10^5$ cells/well) may be co-cultured containing α-MEM and 10% FCS with or without IL-3 for 5-10 days. Vitamin $D_3$ may be used as positive regulator of osteoclastogenesis in co-culture system which is known to increase RANKL expression on osteoblasts. Osteoclast formation may be evaluated by TRAP staining. Mouse AT-MSCs may be isolated from 10- to 12-wks old wild type, STAT5a and STAT5b knockout mice. The proliferation of mouse calvarial osteoblasts in the presence of IL-3 was examined using MTT assay.

The osteoblasts are calvarial osteoblasts and osteoclast precursors are stromal free and macrophage-colony stimulating factor (M-CSF)-dependent osteoclast precursors.

Co-Culturing the Osteoblasts and Osteoclast Precursors Obtained from Step i) and (v) with Cytokine; The calvarial osteoblasts are cultured at density of 1-4×$10^4$ cells/well and osteoclast precursors are cultured at density of 1-4×$10^5$ cells/well for 5-10 days. The calvarial osteoblasts and osteoclasts precursors are co-cultured in a minimal essential medium (α-MEM) containing heat-inactivated fetal calf serum (1-20%), L-glutamine (15 mM), penicillin (20-200 IU/ml), β-glycerophosphate (1-20 mM), and ascorbic acid (20100 μg/ml). The osteoblasts cell and osteoclast precursor cells are incubated at 20-40° C. with 2-10% $CO_2$. Vitamin $D_3$ ($10^{-5}$-$10^{-10}$ M) may be used as a positive control for osteoclastogenesis.

Studying the Effect of IL-3 in Osteoclasts Obtained from Step vi.

To further investigate the molecular mechanism for increase in membrane RANKL by IL-3, osteoblasts may be cultured for 15-120 minutes with IL-3 and activation of JAK2/STAT5 may be evaluated by western blotting. At the functional level not only phosphorylation of STAT5 but also translocation of its phosphorylated form into the nucleus is crucial for its activity. The osteoblasts may be cultured with IL-3 for 30 minutes and STAT5 translocation may be evaluated by immunofluorescence. To further investigate which isoform of STAT5 play a prominent role in IL-3 regulation of RANKL expression, adipose tissue-derived MSCs (AT-MSCs) isolated from wild type, STAT5a and STAT5b knockout mice may be used. AT-MSCs may be cultured for 24 and 48 hours with IL-3 and the expression of RANKL may be analysed at both gene and protein levels. The present invention demonstrates that IL-3 does not significantly increase TRAP, cathepsin K, calcitonin receptor and integrin $β_3$ gene. The present invention demonstrates that IL-3 increases the membrane RANKL and decreases the soluble form of RANKL in the in-vitro osteoblast cultures. The down regulation of soluble RANKL by IL-3 is caused by the down regulation of metalloproteases and matrix metalloproteinases wherein the metalloproteases is a disintegrin and metalloproteinase domains (ADAMs) 10, 17, 19 and matrix metalloproteinase is matrix metalloproteinase (MMP) 3.

In Vivo Effects of IL-3

The present invention discloses that there is differential regulation of RANKL expression with age, and in adults IL-3 may have markedly decreased RANKL expression. IL-3 significantly decreased RANKL and increased OPG in serum. Furthermore, increased RANKL/OPG ratio in adult mice was decreased by IL-3. All these results indicate that IL-3 help in restoring the disturbed RANKL and OPG expression in adult mice.

The present invention discloses that interleukin 3 increases membrane RANKL by activating the JAK2/STAT5 pathway.

The present invention discloses that interleukin 3 decreases soluble RANKL by reducing ectodomain shedding of membrane RANKL through downregulation of metalloproteases mainly a disintegrin and metalloproteinase.

The present invention discloses that interleukin 3 decreases serum RANKL level.

The present invention discloses that interleukin 3 increases the serum OPG level.

The present invention discloses that interleukin 3 restores the increased RANKL/OPG ratio.

The present invention discloses that IL-3 will improve the RANKL/OPG ratio in skeletal disorders by 1 to 5 folds, preferably 2 to 4 folds.

The effective amount of interleukin 3 that may be administered to obtain therapeutic intervention is between 10 and 10,000 units/kg body weight, preferably between 50 and 500 units/kg body weight.

The interleukin-3 of the present invention may be administered subcutaneously, transdermally, intravenously, orally, intranasally, intramuscularly, intraperitoneally, buccally, or rectally.

In yet another embodiment, the present invention discloses the use of Interleukin-3 in bone homeostasis modulation, and intervention in skeletal disorders.

Advantages of the Present Invention i. The present invention demonstrates that IL-3 significantly increases RANKL expression in osteoblast at both gene and protein level but showed no effect OPG expression.

ii. The present invention demonstrates that increased RANKL expression by IL-3 induces mononuclear osteoclasts but not multinuclear osteoclasts.

iii. The present invention demonstrates that IL-3 increases the expression of membrane bound RANKL and simultaneously down-regulate the secretion of soluble RANKL.

iv. The present invention demonstrates that IL-3 decreases soluble RANKL by reducing ectodomain shedding of membrane RANKL through down-regulation of metalloproteases mainly ADAM10, ADAM17, ADAM19 and MMP3.

v. IL-3 restores RANKL expression in adult mice by enhancing bone-specific RANKL and decreasing serum RANKL.

vi. IL-3 increases the serum OPG level in adult mice.

vii. IL-3 restore the decreased RANKL/OPG ratio in adult mice.

viii. The present invention demonstrates that IL-3 increases membrane RANKL by activating JAK2/STAT5 pathway.

ix. The present invention demonstrates that IL-3 differentially regulates two functional forms of RANKL under both in vitro and in vivo conditions.

x. The present invention demonstrates that IL-3 restore RANKL expression in adult mice by enhancing bone specific RANKL and decreasing serum RANKL.

xi. The present invention identifies the role of IL-3 in modulation of pathophysiology of bone remodeling, which can further utilized for treatment of skeletal disorders.

EXAMPLES

The following examples are given by the way of illustration of the present invention and therefore should not be construed to limit the scope of the present invention.

Example 1: Animals

BALB/c mice of 2-5 days, 6-8 wks and one year old were obtained from the Experimental Animal Facility of National Centre for Cell Science, Pune, India. STAT5a [C.129S (B6)$^{Stat5atm1Mam}$/J] and STAT5b [C.129-$^{Stat5btm1Hwd}$/J] knockout mice were obtained from Jackson Laboratories. Water and food were provided ad libitum. All the protocols involving animal use were approved by an Institutional Animal Ethics Committee.

Example 2: Reagents and Culture Conditions

RANKL Ab and fluorochrome-conjugated secondary Abs were obtained from Abcam. Polyclonal Abs for IL-3Rα, OPG, pERK1/2, ERK1/2 pJAK2, JAK2, pSTAT5a/b, STAT5 and β-actin were obtained from Santa Cruz. The HRP-conjugated secondary Abs was from Bangalore Genei. Fluorochrome-conjugated anti-mouse IL-3Rα Ab was obtained from Biolegend. Recombinant mouse IL-3 was obtained from BD Biosciences. 1α,25dihydroxyvitamin $D_3$ was obtained from Sigma. FCS, L-glutamine, TRIzol reagent, cDNA synthesis kit, and SYBR Green were obtained from Invitrogen. Collagenase and dispase were purchased from MP Biomedicals. RANKL and OPG ELISA kits were obtained from R&D system.

All cultures were incubated in growth medium containing α-MEM, heat-inactivated FCS (10%), L-glutamine (2 mM), penicillin (100 IU/ml), streptomycin (100 µg/ml); and osteogenic factors, β-glycerophosphate (10 mM) and ascorbic acid (50 µg/ml, all from Sigma-Aldrich). All incubations were performed at 37° C. in a humidified atmosphere of 5% $CO_2$ in air.

Example 3: Isolation of Calvarial Osteoblasts

Mouse calvarial osteoblasts were isolated from 2 to 5 days old BALB/c mice using modified sequential digestion method as described previously (31). Briefly, surgically resected calvariae were cleaned off adherent soft tissues and subjected to five sequential (5, 15, 10, 10 and 5 min) digestions in enzyme solution containing 0.1% collagenase and 0.2% dispase at 37° C. Cells released from $2^{nd}$ to $4^{th}$ digestions were pooled, centrifuged and resuspended in growth medium as described above. Calvarial osteoblasts of passage 2 were used in all the experiments.

Example 4: Isolation of Bone Marrow-Derived Osteoclast Precursors

Stromal cells free and M-CSF-dependent osteoclast precursors were isolated from 6 to 8 wks old BALB/c mice as previously described (25). Briefly, femoral and tibial bones were aseptically removed and cleaned by removing adherent soft tissues. The bone ends were cut, and the bone marrow cavity was flushed out with α-MEM from one end of the bone using a sterile 21-gauge needle. Bone marrow cells were washed twice and incubated for 24 h in the presence of M-CSF (10 ng/ml) at a density of $3 \times 10^5$ cells/ml in a 75-cm$^2$ flask. After 24 h, nonadherent cells were collected and layered on a Ficoll-Hypaque (Sigma-Aldrich) gradient. Cells at the gradient interface were collected, washed twice, and used for further experiments.

Example 5: Co-Culture Model for Osteoclastogenesis

To evaluate the effect of IL-3 on osteoclast differentiation in co-culture model, mouse calvarial osteoblasts ($2 \times 10^4$ cells/well) and bone marrow-derived osteoclast precursors ($2 \times 10^5$ cells/well) were co-cultured in 48 well plates containing α-MEM and 10% FCS with or without IL-3 for 7 days (32). Vitamin $D_3$ was used as positive regulator of osteoclastogenesis in co-culture system which is known to increase RANKL expression on osteoblasts. Osteoclast formation was evaluated by tartrate-resistant acid phosphatase (TRAP) staining.

Example 6: Isolation of Adipose Tissue-Derived MSCs (AT-MSCs)

Mouse AT-MSCs were isolated from 10- to 12-wks old wild type, STAT5a and STAT5b knockout mice as described previously (33). Briefly, subcutaneous adipose tissue was digested with 2 mg/ml collagenase (type 1A, Sigma-Aldrich) in PBS at 37° C. for 15-20 min. The cell suspension obtained was centrifuged, resuspended in α-MEM containing 10% FCS and seeded in culture flask. After 72 hours non-adherent cells were discarded and adherent cells were cultured until they attained 80-90% confluency. Homogenous populations of ATMSCs from passage 2 or 3 were used in all further experiments.

Example 7: MTT Assay

The proliferation of mouse calvarial osteoblasts in the presence of IL-3 was examined using MTT assay. After incubation period, cell culture media was replaced with 100 µl of MTT (0.5 mg/ml) solution and cells were further incubated at 37° C. for 3-4 hours. The MTT solution was removed and formazan crystals formed were dissolved in 100 µl of DMSO. The absorbance was measured at 570 nm.

Example 8: Quantitative Real Time-Polymerase Chain Reaction

Expression of RANKL, OPG, M-CSF, ADAM10, ADAM17, ADAM19, MMP3, MMP14, TRAP, Cathepsin K, calcitonin receptor, integrin $β_3$ and GAPDH was assessed by real time PCR analysis. RNA was isolated from cells by TRIzol reagent method (Invitrogen). 2 µg of total RNA was used for synthesis of cDNAs by reverse transcription (cDNA synthesis kit). For real-time PCR, a 10-µl reaction mixture containing SYBR Green and 10 pmol of each primer was used and PCR was set using StepOnePlus (trademark) system (Applied Biosystems). The amplification was performed using 1 cycle of 95° C. for 10 min and 40 cycles of denaturation at 95° C. for 15 s, primer annealing and extension at 60° C. for 60 s, followed by melt curve analysis. The primer sequences (IDT) used are summarized in Supplementary Table 51. Each reaction was run in duplicates and Data was analyzed for fold change using comparative $2^{-\Delta\Delta CT}$ method.

Example 9: Immunofluorescence Microscopy

Mouse calvarial osteoblasts were cultured on glass coverslips in 24-well plates in the absence or presence of IL-3 for indicated time points. The cells were washed twice with PBS, fixed with 4% paraformaldehyde for 10 min and permeabilized with 0.1% Triton X-100 in PBS for 5 min. Staining for RANKL, OPG and IL-3Rα was carried out using primary Abs followed by fluorochrome conjugated secondary Abs. After washing cells were mounted using Dabco (Sigma-Aldrich) and viewed with a Zeiss LSM 510 confocal microscope equipped with argon and helium lasers (Zeiss).

Example 10: Flow Cytometry

Cells were cultured with or without IL-3 for indicated time points. At the end of culture period adherent cells were harvested from culture dishes using cell dissociation buffer (Life Technologies), and few remaining cells were dislodged by gentle scraping on ice. Cell surface staining was performed by incubating $10^5$ cells in 100 µl PBS with fluorochrome conjugated Abs. For intracellular staining cells were first permeabilized with perm buffer (0.1% Triton-X in 1×PBS) then stained with RANKL and OPG Abs. Cells were washed, acquired and analyzed with BD FACSCalibur (trademark). Data was analyzed using CellQuest (trademark) Pro software (Becton-Dickinson). The results are expressed as percentage of cells and delta mean fluorescence intensity (ΔMFI).

Example 11: ELISA

Cell culture supernatants were harvested after indicated time of incubation, centrifuged and immediately frozen at −80° C. until further analysis. All samples were thawed immediately prior to evaluation by ELISA. Soluble RANKL and OPG proteins were measured in supernatant and serum using respective Quantikine mouse ELISA kits. The procedure was carried out according to the manufacturer's instructions and the absorbance was measured at 450 nm with a correction wavelength of 540 nm.

Example 12: Western Blotting

Cells were seeded at a density of $5 \times 10^4$ cells/cm² in α-MEM containing 10% FCS and cultured for indicated time periods in absence or presence of IL-3. The cells were lysed in RIPA buffer containing protease inhibitors, and proteins were estimated using BCA method. Protein samples were then subjected to 12% SDS-PAGE. The proteins were transferred from gels onto a nitrocellulose membrane for immunoblot analysis. Blocking was performed with 5% non-fat dry milk in TBS buffer. The membrane was then incubated with primary Ab (1:1000) for 3 h. After washing, the membranes were incubated with HRP-conjugated secondary Abs, and labeled proteins were detected using ECL reagents (Amersham Biosciences). Relative intensities of protein bands were analysed by densitometry using ImageJ software.

Example 13: Tartrate-Resistant Acid Phosphatase (TRAP) Staining

Cells were washed gently in PBS and fixed in 10% formalin for 10 minutes at RT. TRAP staining was performed at 37° C. for 10-15 minutes by incubating cells in TRAP buffer (70 mM sodium acetate, 30 mM acetic acid, 0.1 mg/ml naphthol AS-MX phosphate disodium salt, 0.1% Triton X-100 at pH 5.0). Number of TRAP-positive mononuclear and multinuclear (three or more nuclei) osteoclasts was counted.

Example 14: In Vivo Analysis of RANKL and OPG

To investigate the in vivo role of IL-3 on RANKL and OPG expression, young mice of three months old and adult mice of one year old were used. Adult mice were injected intraperitoneally with PBS or IL-3 (3 µg/mouse/day) for 5 days. Young mice injected with PBS were used as a control to compare the changes in RANKL and OPG with adult mice. On day six bone and serum samples were collected. Bone specific RANKL expression was analyzed by immunoblotting from femur and tibia bones after removal of bone marrow. Serum RANKL and OPG levels were analyzed by ELISA.

Example 15: Statistical Analysis

Results are represented as mean±SEM. Statistical significance was calculated using one-way ANOVA with a subsequent post hoc Bonferroni's test for multiple comparisons. The significance values are defined as $*p$ or $^{\#}p \leq 0.05$; $p$ or $^{\#\#}p \leq 0.01$ and $*p$ or $^{\#\#\#}p \leq 0.001$.

We claim:

1. A method of providing therapeutic intervention against osteoporosis which method comprises administering to a mammal in need thereof a therapeutically effective amount of interleukin 3 in an amount of between 50 and 500 units/kg body weight.

2. The method of claim 1, wherein said interleukin 3 is human interleukin 3.

3. The method of claim 1, wherein said interleukin 3 increases membrane receptor activator of nuclear factor kappa-B ligand (RANKL) by activating a pathway mediated by janus kinase 2/signal transducer and activator of transcription 5 (JAK2/STAT5).

4. The method of claim 1, wherein said interleukin 3 decreases soluble RANKL by reducing ectodomain shedding of membrane RANKL through downregulation of a disintegrin and metalloprotease (ADAM).

5. The method of claim 1, wherein said interleukin 3 decreases serum RANKL level.

6. The method of claim 1, wherein said interleukin 3 increases serum osteoprotegerin (OPG) level.

7. The method of claim 1, wherein said interleukin 3 restores an increased RANKL/OPG ratio in the mammal.

8. The method of claim 1, wherein an RANKL/OPG ratio is improved in the mammal by 1 to 5 folds.

9. The method of claim 8, wherein the RANKL/OPG ratio is improved in the mammal by 2 to 5 folds.

10. The method of claim 1, wherein said interleukin-3 is administered subcutaneously, transdermally, intravenously, orally, intranasally, intramuscularly, intraperitoneally, buccally, or rectally.

11. A method of modulating bone homeostasis for therapeutic intervention of a bone disorder which method comprises administering to a mammal in need thereof a therapeutically effective amount of interleukin 3 in an amount of between 50 and 500 units/kg body weight.

* * * * *